United States Patent [19]

Pitha et al.

[11] Patent Number: 4,877,774
[45] Date of Patent: Oct. 31, 1989

[54] ADMINISTRATION OF STEROID HORMONES

[75] Inventors: Josef Pitha, Baltimore; Mitchell Harman, Ellicott City, both of Md.; Kaneto Uekama, Kumamoto, Japan

[73] Assignee: The United States of America as represented by the Department of Health and Human Services, Washington, D.C.

[21] Appl. No.: 94,597

[22] Filed: Sep. 9, 1987

[51] Int. Cl.$^4$ ................. A61K 31/70; A61K 31/56
[52] U.S. Cl. .................................. 514/26; 514/58; 514/946; 514/960; 514/178
[58] Field of Search ............. 514/58, 946, 960, 178, 514/26

[56] References Cited

U.S. PATENT DOCUMENTS

| 4,054,736 | 10/1977 | Hayashi et al. | 514/826 |
| 4,378,995 | 10/1984 | Shinoda et al. | 514/58 |
| 4,383,992 | 5/1983 | Lipari | 514/58 |
| 4,438,106 | 3/1984 | Wagu et al. | 514/58 |
| 4,518,588 | 5/1985 | Szejtli et al. | 514/58 |
| 4,663,316 | 5/1987 | Ninger | 514/99 |
| 4,670,419 | 6/1987 | Uda et al. | 514/806 |
| 4,727,064 | 2/1988 | Pitha | 514/965 |

FOREIGN PATENT DOCUMENTS

| 60-92221 | 6/1981 | Japan | 514/58 |
| 7024312 | 2/1982 | Japan | 514/58 |
| 8099437 | 6/1983 | Japan | 514/58 |
| 9046228 | 3/1984 | Japan | 514/58 |
| WO85/02767 | 7/1985 | PCT Int'l Appl. | 514/58 |

OTHER PUBLICATIONS

Kempfle et al., "The Binding of Fluorescent Steroids to Cyclodextrins as Models for Steroid Protein Interaction", Chem. Abst. 106:113678, 1987.
Kempfle et al, "Fluorecent Steroids–Interactions with Cyclodextrins", Chem. Abst. 101:17560, 1984.
"Inclusion Complexations of Steroid Hormones with Cyclodextrins in Water and in Solid Phase", Uekama et al, Int. J. Pharm 10(1982): 1–15.

Primary Examiner—H. M. S. Sneed
Assistant Examiner—J. Saba
Attorney, Agent, or Firm—Browdy and Neimark

[57] ABSTRACT

Crystalline complexes of steroid hormones with gamma-cyclodextrin are prepared by mixing the components together. Tablets can be formed from the complexes, which can be administered by contact with the mucosa to provide effective transfer of the hormones into the systemic circulation, gradually eliminating the hormones therefrom.

10 Claims, 2 Drawing Sheets

ADMINISTRATION OF STEROID HORMONES

FIELD OF THE INVENTION

The present invention relates to a pharmaceutical form for sublingual administration of hormones.

BACKGROUND OF THE INVENTION

Therapeutic use of steroidal hormones is required in the treatment of a number of diseases, including lack of natural hormones, osteoporosis, and premenstrual syndrome. However, effective treatment is difficult, since these steroids are absorbed only slowly from the gastrointestinal tract, and are rapidly cleared from circulating blood by the liver.

Numerous attempts have been made to circumvent these problems, including the administration of huge doses of natural hormones orally or preparations of oil solutions of hormones which are injected intramuscularly, and synthesis of analogs of natural hormones. The latter approach provides active preparations which may have significant side effects. Administration of these hormones transdermally or by nasal sprays has also been suggested, but these methods have not met with great acceptance. The optimal method for the administration of steroidal hormones would use noninvasive entry of physiological amounts of chemically unmodified hormones, and would lead to normal levels of hormones in the circulation. Furthermore, such a method should be adaptable for mass use.

Deficiency of steroidal hormones in the elderly is a problem of particularly serious consequences. In postmenopausal women, unless corrected, this deficiency leads to osteoporosis, which, in the United States, is blamed for over one million bone fractures annually. In men, the production of testosterone does not dramatically decrease with age, but the amount of testosterone binding globulin increases and thus, in some men, hormonal supplementation is needed.

Steroidal hormones are readily available, and supplementation by natural compounds can be used. However, oral administration of these steroids is complicated by their lack of solubility, which delays their absorption until they reach the lower gastrointestinal tract, where metabolism by the portal vein-liver system, i.e., first-pass effect, and degradation by microbial flora are problems.

The use of hydrophilic cyclodextrin derivatives in pharmaceutical preparations of steroid hormones has been disclosed in Pitha, U.S. Pat. No. 4,596,795. Amorphous hydrophilic derivatives of beta- and gamma-cyclodextrins seemed to give better results than any of the parent cyclodextrins for the solubilization of steroid hormones, a step which appears to be crucial for their absorption by tissues. In a human trial, amorphous derivatives of beta-cyclodextrins enabled effective administration of testosterone, estradiol, or progesterone under conditions when improvements obtainable with beta-cyclodextrin alone were marginal.

Hayashi et al., in British application No. 2,104,907A, disclose cyclodextrin inclusion compounds wherein at least one guest compound selected from the group consisting of eicosapentaenoic acid and docosahexaenoic acid is included. The guest compound reduces cholesterol levels in human serum, and the inclusion compound can be incorporated for this purpose in pharmaceutical compositions.

Jones, in U.S. Pat. No. 4,555,504, disclose inclusion compounds of cyclodextrins and cardiac glycosides which have high aqueous solubility and can be used for preparing pharmaceutical formulations containing cardiac glycosides for use in therapy. The preferred cyclodextrin is beta-cyclodextrin.

Szejtli et al., in U.S. Pat. No. 4,524,068, disclose a cyclodextrin inclusion complex of piperonyl butoxide. In this case, the complex is prepared by reacting cyclodextrin or an aqueous or non-aqueous solution thereof with piperonyl butoxide. The cyclodextrin complexes are said to synergize the pesticidal effect of known insecticides and fungicides to a greater extent than piperonyl butoxide.

Szejtli et al., in U.S. Pat. No. 4,380,626, disclose inclusion compounds of 2-chloro ethyl phosphonic acid formed with an alpha-, beta-, or gamma-cyclodextrin or mixtures thereof. These complexes can be used for preparing plant growth regulating compositions.

Pitha et al., in J. Pharm. Sci. 75, No. 2, February, 1986, 165–167, disclose that condensation products of beta-cyclodextrin with propylene oxide or epichlorohydrin, which are amorphous and thus very soluble in water, can be used to form complexes with testosterone, progesterone, and estradiol.

Cyclodextrins are products of the enzymatic degradation of starch, and contain six to eight glucose units joined in a ring by alpha-1→4 glycosidic bonds. They are known to solubilize nonpolar compounds and improve the absorption of drugs from the gastrointestinal tract. Nevertheless, beta-cyclodextrin itself has proven unsuitable for improving the absorption of drugs.

The lack of toxicity of the cyclodextrins has already been documented using animals.

It has been observed that steroidal hormones are present in the serum only when the drug is absorbed into the bloodstream in such a means that the portal vein is bypassed. This is in accordance with the fast metabolism of steroidal hormones in the liver. The half-lives of these hormones in the circulatory system are estimated to be in minutes. The direct route into the bloodstream bypassing the portal vein is known to be less immediately affected by liver metabolism than entry from the gastrointestinal tract. Furthermore, metabolism of the drug by intestinal tissue is avoided.

SUMMARY OF THE INVENTION

It is an object of the present invention to avoid the above-described deficiencies in the prior art.

It is another object of the present invention to provide a composition for direct administration of steroid hormones across the mucosa.

It is yet a further object of the present invention to provide compositions for effective administration of steroid hormones.

It has been found that the rapid dissolution and rapid reversibility of formation found in some inclusion complexes of steroids permits efficient absorption of hormones directly into the bloodstream while bypassing the portal vein system, including sublingually, buccally, rectally, or ocularly. This direct absorption of hormones is highly desirable, since then the hormone is less subject to rapid metabolism by the portal vein-liver system, and relatively long periods of hormone levels in circulation may be obtained in this manner. The only other known way to avoid first pass effects in oral administration is by administering a prodrug of hormone together with lipids into the lymphatic system. Previously, effective absorption of steroid hormones from the oral cavity was obtained only by using amorphous, rather than crystalline, complexes with cyclodextrin derivatives. However, the present invention has demonstrated that even dissolution of some crystalline complexes may be sufficient for reasonable absorption to occur.

According to the present invention, a solid complex is formed from a steroid hormone and gamma-cyclodextrin by mixing appropriate amounts of the steroid hormone and gamma-cyclodextrin in water. The appropriate proportions in the mixture can be determined by examining the descending curvature of the $B_s$-type phase solubility of FIG. 1.

For example, 1 gram of testosterone and 57 grams of gamma-cyclodextrin were added to 500 ml of water, and the mixture was stirred at 25° C. for seven days. The complex, which precipitated as a microcrystalline powder, was removed by filtration and dried under vacuum at room temperature for 24 hours. This powder corresponded to a 1:2 testosterone:gamma-cyclodextrin complex, which had a molecular weight of 2882.

The complexes of the present invention are transported into the bloodstream directly by direct administration across the mucous membranes or the conjunctiva in the body for immediate absorption into the bloodstream. For the purposes of the present invention, direct administration against the mucous membranes, or mucosa, means that the active ingredient with optional fillers or excipients is administered by direct contact with the mucosa. This, of course, would exclude oral administration by swallowing, as the active ingredient there would not necessarily be indirect contact with the mucosa, and the active ingredient is transported directly to the portal vein. These complexes thus are preferentially administered buccally, sublingually, rectally, or ocularly.

DETAILED DESCRIPTION OF THE INVENTION

Complexes of steroidal hormones with gamma-cyclodextrin are prepared by stirring the components for several days in aqueous suspension. The resulting complexes contain about 10% steroid. Tablets were made from pulverized complexes, and these tablets, when administered sublingually, resulted in a markedly elevated hormonal level in the human subject. Dissolution of the tablet under the tongue occurred within 10 to 15 minutes. When the complex was dissolved in water and administered by stomach tube, elevation of the hormones in the serum was minimal.

Figure 1:
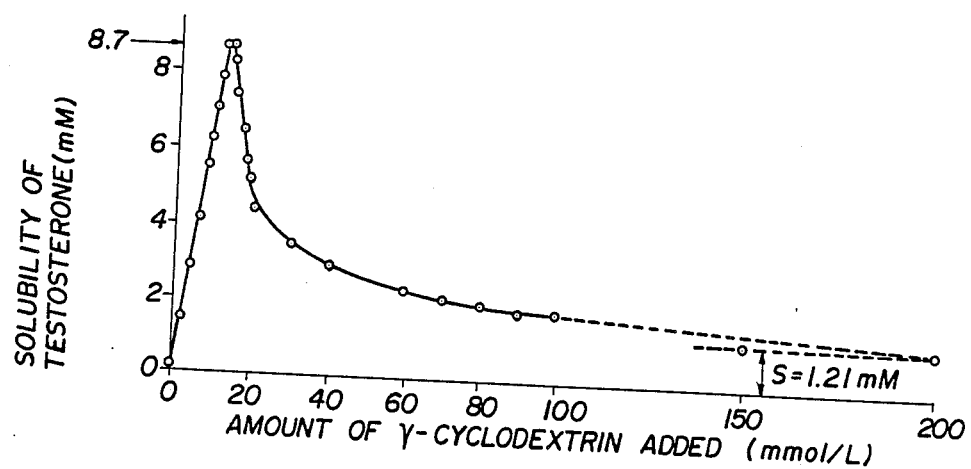
FIG. 1 shows the phase-solubility diagram of a testosterone-gamma-cyclodextrin system in water at 25° C.

The solid complex of testosterone and gamma-cyclodextrin was prepared by mixing the appropriate amounts of testosterone and gamma-cyclodextrin in water. The appropriate mixture was determined by examining the descending curvature of the $B_s$-type phase solubility diagram, as shown in FIG. 1. By way of example, one gram of testosterone and 57 grams of gamma-cyclodextrin were added to 500 ml of water, and the mixture was stirred at 25° C. for seven days. The complex, which precipitated as a microcrystalline powder, was removed by filtration and dried under vacuum at room temperature for 24 hours. This powder corresponded to a 1:2 testosterone-gamma-cyclodextrin complex, which had a molecular weight of 2882.

The composition of the present invention was administered to a 53-year-old male with hypopituitarism which had been diagnosed when he was 47. The subject had used a daily supplement of thyroxine, and the experiments were performed just before the subject was supplemented with the depo form of testosterone, when his testosterone levels were subnormal. The subject swallowed a stomach tube, size 18Fr, total length 50 inches, to simulate fasting conditions for the administration of liquids into the subject. The position of the tube was ascertained by the subject's reaction to the rapid introduction of 50 ml. of air into the tube, and measuring the acidity of liquid aspirated therefrom to identify stomach juice.

The phase-solubility diagram of the testosterone-gamma-cyclodextrin system in water, FIG. 1, is of the $B_s$-type, i.e., a complex of limited solubility is formed. A complex containing both components began to crystallize out from the solution when the concentration of gamma-cyclodextrin reached about 13 mM, a concentration which is lower than the solubility of gamma-cyclodextrin itself, 168 mM. The concentration of testosterone in the solution varied from that in water (0.13 mM, 37 micrograms/ml) through a maximal solubilization of 8.7 mM (2.5 mg/ml) to that of limit value (1.21 mM, 350 micrograms/ml). The isolated complex contained 10% testosterone by weight, i.e., one molecule of testosterone for two molecules of gamma-cyclodextrin.

Figure 2:
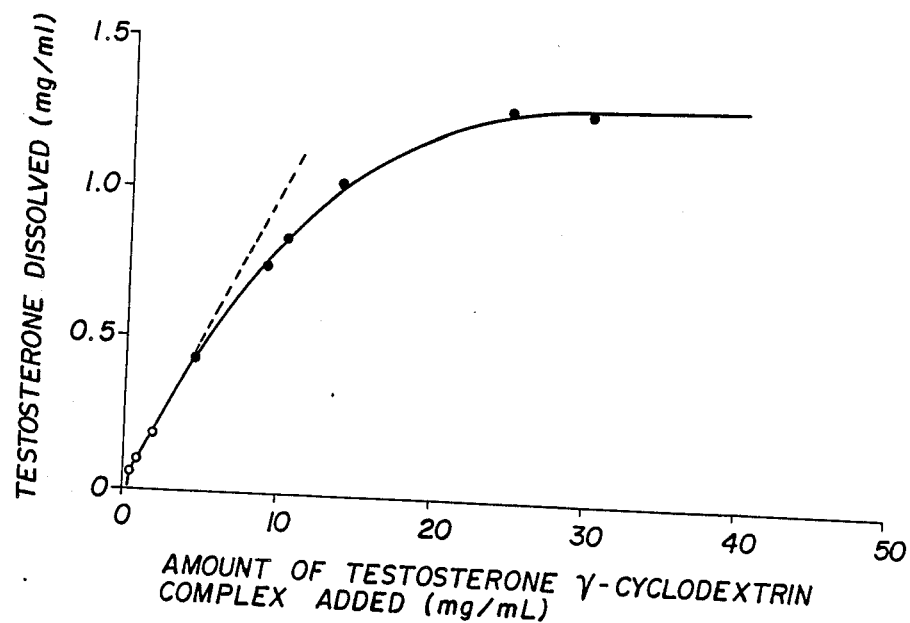
FIG. 2 shows a phase-solubility diagram of the crystalline testosterone-gamma-cyclodextrin complex in water system at 20° C. Regions of incomplete solubility are indicated by solid points.

When the crystalline complex was equilibrated with water, a full dissolution occurred up to about 4 mg/ml (i.e., 0.4 mg/ml of testosterone), and at that point the concentration of dissolved testosterone was close to the limit value above. When further amounts of crystalline complex were added, incomplete dissolution occurred. The phase-solubility diagram of FIG. 2 is somewhat rounded, thus suggesting the possibility of several components in the system. Thus, for example, both 1:1 and 1:2 complexes may be formed, the latter with a lower solubility, as seen in FIG. 1. When that complex is again dissolved in water, it partially reverts to a 1:1 complex. Incomplete dissolution may be due to the formation of equilibria involving less soluble components. The maximal concentrations of testosterone obtainable with the crystalline complex were about 4.5 mM (1.3 mg/ml). That solubilization is considerably lower than those obtained with amorphous cyclodextrin derivatives, namely, 2-hydroxypropyl-beta-cyclodextrin or poly-beta-cyclodextrin.

Figure 3:
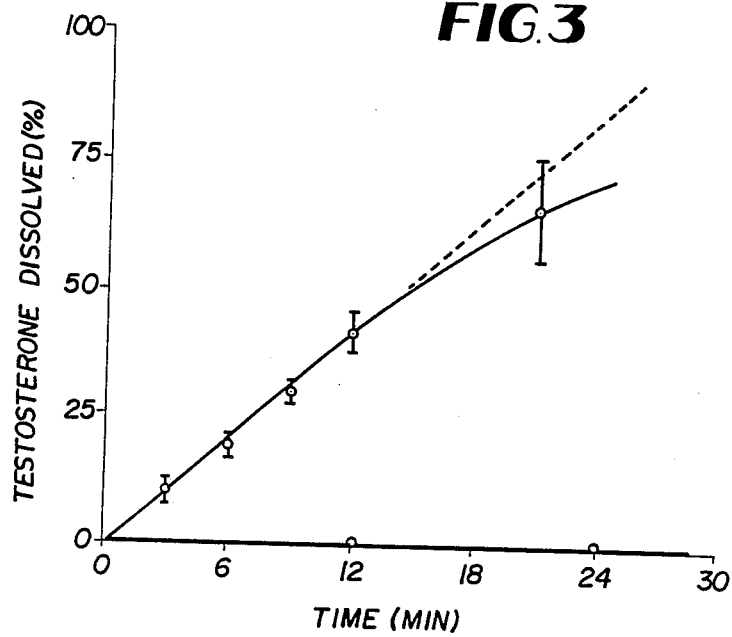
FIG. 3 shows the rate of dissolution of a tablet (100 mg) containing crystalline testosterone:gamma-cyclodextrin complex in water (200 ml, 20° C.) (open circles); and dissolution rate of testosterone from a similar tablet made from testosterone-cellulose mixture (solid points).

The crystalline complex of the present invention can be directly processed into tablet form in a manner similar to other complexes. The tablets may contain any pharmaceutically acceptable fillers or excipients which are appropriate for the intended use of the tablets. These tablets dissolved completely in an appropriate volume of water, with a rate of testosterone release which was orders of magnitude higher than the dissolution of testosterone from a tablet containing cellulose as the excipient, cf. FIG. 3. Nevertheless, the release of testosterone from tablets of gamma-cyclodextrin complex was at about a ten times lower rate than tablets of a testosterone-hydroxypropyl-beta-cyclodextrin complex.

Figure 4:
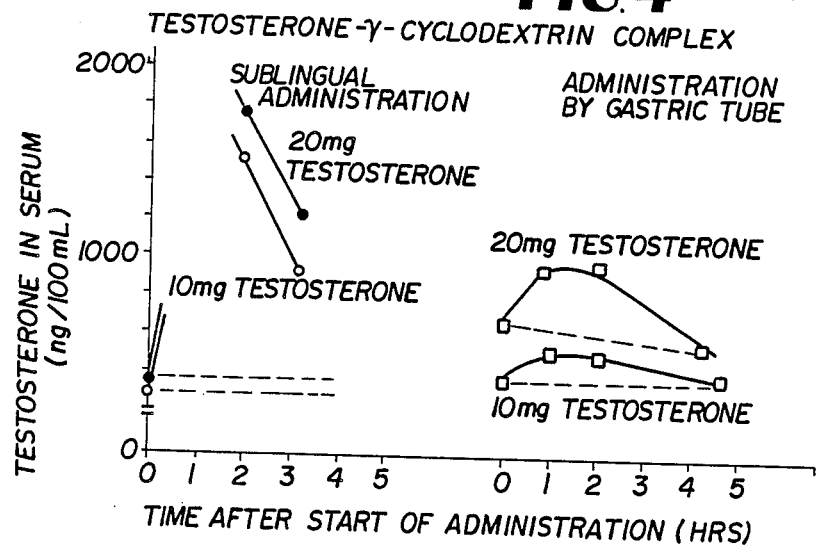
FIG. 4 shows the serum level of testosterone after administration of tablets or solution of crystalline testosterone:gamma-cyclodextrin complex to a human sublingually.

When tablets of testosterone-gamma-cyclodextrin complex were administered sublingually, their full dissolution was rather slow (10–15 minutes) when compared to previously evaluated preparations. However, these tablets provided an efficient transfer of the hormone into the circulation, as shown in FIG. 4. The half-life of testosterone thus introduced into the circulation was about one hour, which was comparable to that observed with the testosterone-hydroxypropyl-beta-cyclodextrin complex administered in the same way. When solutions of testosterone and gamma-cyclodextrin complex were introduced in similar amounts by a gastric tube directly into the stomach, serum levels of hormone were much lower, as can be seen in FIG. 4. Similarly, when the complex was administered into the stomach in a dry form using hard gelatin capsules, transfer into the circulating blood was much lower than after sublingual administration, as shown in FIG. 4.

Corresponding complexes of 1 mg estradiol with gamma-cyclodextrin and 20 mg progesterone with gamma-cyclodextrin, prepared as above, were tested on a male volunteer. One hour after administration, the serum level of estradiol was 40.4 ng/dL, and progesterone level was 940 ng/dL.

The rapid dissolution and rapid reversibility of formation which is found in some inclusion complexes of steroids enables efficient absorption of hormones from the oral cavity. Absorption of hormones through the mucosa or conjunctiva is highly desirable, since the hormone is not as much the subject of rapid metabolism by the portal vein-liver system, and relatively long periods of hormone levels in circulation may be obtained in this manner. The only other way to avoid first pass effects in per os administration is by administering a prodrug of the hormone together with lipids into the lymphatic system. Previously, effective absorption of steroid hormones from the oral cavity was obtained only by using amorphous, but not crystalline, complexes with cyclodextrin derivatives. The present results demonstrate that even dissolution of some crystalline complexes is sufficient for reasonable absorption to occur.

The dissolution rates of testosterone alone or its release from complexes of interest were measured and compared with published data. These dissolution rates can be arranged in a scale with the relative order: testosterone 1 < testosterone:beta-cyclodextrin complex 3 < testosterone:gamma-cyclodextrin complex 33 < testosterone:poly-beta-cyclodextrin complex 330 ≅ testosterone:2-hydroxypropyl-beta-cyclodextrin complex 330. The effects of complexation on testosterone solubility can be compared on an absolute scale:testosterone, 37 micrograms/ml < testosterone:beta-cyclodextrin comples, 23 micrograms/ml < testosterone:gamma-cyclodextrin complex, 350 micrograms/ml < testosterone:poly-beta-cyclodextrin complex or testosterone:2-hydroxypropyl-beta-cyclodextrin complexes, which can be dissolved to 30,000 micrograms/ml. Previous evaluations of absorption from the oral cavity and the present data indicate that the demarkation line for effectiveness is close to, but includes, the testosterone-gamma-cyclodextrin complex. Solubilization to about 1 mM and a dissolution rate of about 5 micromoles/min may be satisfactory for the drug form to be administered sublingually.

In contrast to beta-cyclodextrin and to chemically modified cyclodextrin complexes, the presently used gamma-cyclodextrin is susceptible to the amylases of human saliva. The hydrolysis yields products which do not complex or solubilize testosterone. The data presented here and their comparison with published data show that this hydrolysis does not preclude the successful use of this hydrolyzable carbohydrate in sublingual tablets.

The crystalline complexes of steroid hormone with gamma-cyclodextrin can be used to treat a variety of conditions, including testosterone replacement in hypogonadism, progesterone replacement and therapy, testosterone supplementation of male contraception, and estradiol replacement and therapy.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for administering steroid hormones to a patient needing supplemental steroid hormones by direct contact with mucosa or the conjuctiva comprising contacting the mucosa of said patient needing supplemental steroid hormones with an effective amount of a steroid hormone complexed with crystalline gamma-cyclodextrin.

2. The method of claim 1 wherein the steroid hormones are selected from the group consisting of testosterone, estradiol, and progesterone.

3. The method of claim 2 wherein the steroid hormone is testosterone.

4. A method of treating a mammal needing supplemental steroid hormones by administering steroid hormones comprising contacting the mucosa of said mammal needing supplemental steroid hormones with an effective amount of a crystalline complex of a steroid hormone with gamma-cyclodextrin.

5. The method of claim 4 wherein the steroid hormone is selected from the group consisting of testosterone, estradiol, and progesterone.

6. The method of claim 5 wherein the steroid hormone is testosterone.

7. The method of claim 1 wherein the complex is administered sublingually.

8. The method of claim 1 wherein the complex is administered buccally.

9. The method of claim 1 wherein the complex is administered rectally.

10. The method of claim 1 wherein the complex is administered ocularly.

* * * * *